US009757093B2

(12) United States Patent
Taki et al.

(10) Patent No.: US 9,757,093 B2
(45) Date of Patent: Sep. 12, 2017

(54) OBJECT INFORMATION ACQUIRING APPARATUS AND CONTROL METHOD FOR SAME

(71) Applicant: CANON KABUSHIKI KAISHA, Tokyo (JP)

(72) Inventors: Hirofumi Taki, Kyoto (JP); Kenichi Nagae, Yokohama (JP); Toru Sato, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 307 days.

(21) Appl. No.: 14/156,554

(22) Filed: Jan. 16, 2014

(65) Prior Publication Data

US 2014/0206998 A1 Jul. 24, 2014

(30) Foreign Application Priority Data

Jan. 23, 2013 (JP) ................................. 2013-010410

(51) Int. Cl.
*A61B 8/00* (2006.01)
*G01S 7/52* (2006.01)
(Continued)

(52) U.S. Cl.
CPC .................. *A61B 8/54* (2013.01); *A61B 8/14* (2013.01); *A61B 8/5207* (2013.01);
(Continued)

(58) Field of Classification Search
CPC .... A61B 8/00; A61B 8/14; A61B 8/54; A61B 8/5207; A61B 8/0891; G01S 15/8915; G01S 15/52047
See application file for complete search history.

(56) References Cited

U.S. PATENT DOCUMENTS

| 5,908,391 A | 6/1999 | Muzilla et al. ............... 600/454 |
| 2007/0198203 A1 | 8/2007 | Kumira ........................... 702/85 |

(Continued)

FOREIGN PATENT DOCUMENTS

| JP | 2007-244848 | 9/2007 |
| JP | 2010-183979 | 8/2010 |

OTHER PUBLICATIONS

H. Taki et al., "High Range Resolution Medical Acoustic Vascular Imaging with Frequency Domain Interferometry", *Conf. Proc. IEEE Eng Med Biol Soc.* 2010, 1, pp. 5298-5301 (Aug.-Sep. 2010).

(Continued)

*Primary Examiner* — Peter Luong
(74) *Attorney, Agent, or Firm* — Fitzpatrick, Cella, Harper & Scinto (57) ABSTRACT

Provided is an object information acquiring apparatus including elements with which an acoustic wave is transmitted to and received from an object and converted into a plurality of received signals, a processor that acquires a power intensity signal of the inside of the object, and a corrector that corrects the power intensity signal, the processor being configured to calculate correlation values of frequency components, perform frequency average processing on a correlation matrix that is a set of the plurality of calculated correlation values to acquire a first power intensity signal, and reduce variance of elements in the diagonal direction of the correlation matrix to acquire a second power intensity signal, and the corrector being configured to output a power intensity signal subjected to correction processing.

20 Claims, 8 Drawing Sheets

(51) Int. Cl.
   *G01S 15/89*   (2006.01)
   *A61B 8/14*   (2006.01)
   *A61B 8/08*   (2006.01)

(52) U.S. Cl.
   CPC ...... *G01S 7/52047* (2013.01); *G01S 15/8915* (2013.01); *A61B 8/0891* (2013.01)

(56) References Cited

U.S. PATENT DOCUMENTS

| | | | |
|---|---|---|---|
| 2011/0208035 A1 | 8/2011 | Baba et al. | 600/407 |
| 2011/0307181 A1 | 12/2011 | Nagae | 702/19 |
| 2012/0259218 A1* | 10/2012 | Nagae | A61B 8/085 600/437 |
| 2012/0314534 A1 | 12/2012 | Yoda et al. | 367/7 |
| 2014/0051970 A1 | 2/2014 | Ebisawa et al. | 600/407 |
| 2014/0056105 A1 | 2/2014 | Nagae et al. | 367/87 |

OTHER PUBLICATIONS

H. Taki et al., "High Resolution Medical Acoustic Vascular Imaging Using Frequency Domain Interferometry", *Ninth IASTED International Conference on Visualization, Imaging and Image Processing (VIIP)*, pp. 7-12 (Jul. 13, 2009).

Office Action issued on Apr. 30, 2015 in counterpart P.R. China application 201410023643.8, with translation.

S. Tanigawa et al., "Direction-of-Arrival Estimation of Speech Using Virtually Generated Multichannel Data from Two-Channel Microphone Array", *Electronics and Communications in Japan*, Part 3, vol. 86, No. 2, pp. 33-42 (Feb. 2002).

N. Purswani et al., "Active Cancellation of Probing in the Presence of Multiple Coherent Desired Radar Sources", *IEEE Applied Electromagnetics Conference 2009*, pp. 1-4 (Dec. 14, 2009).

Extended European Search Report issued on Jan. 20, 2015, in counterpart EPA 14150397.9.

* cited by examiner

OBJECT INFORMATION ACQUIRING APPARATUS AND CONTROL METHOD FOR SAME

BACKGROUND OF THE INVENTION

Field of the Invention

The present invention relates to an object information acquiring apparatus and a control method for the same.

Description of the Related Art

In an ultrasound wave diagnostic apparatus that achieves medical ultrasound wave imaging, it is possible to generally represent the spatial resolution in the depth direction, in the case where an image is formed by pulse echo method, by $(n\lambda)/2$, where $\lambda$ is the wavelength of an ultrasound wave and n is the number of transmitted waves. For example, the spatial resolution in the case where two wavelengths of ultrasound waves with a center frequency of 12 MHz have been transmitted is approximately 0.13 mm.

The pulse echo method will be described. First, when an ultrasound wave pulse (elastic wave) is transmitted to an object by a probe or the like, an ultrasound wave is reflected back in accordance with the acoustic impedance within the object. Next, this reflected wave is received, and an envelope of the waveform of the reflected wave is acquired. By the envelope being converted into and displayed in a brightness value, brightness information on a scanning line in a direction in which the ultrasound wave has been transmitted and received is obtained. By repeating transmission and reception of an ultrasound wave with respect to a plurality of directions or positions within the object, brightness information on a plurality of scanning lines can be acquired. By arranging the brightness information on the a plurality of scanning lines, imaging of the inside of the object is possible. Generally, in an ultrasound wave diagnostic apparatus, a plurality of ultrasound wave/electricity converting elements are used, and a temporal difference between the waveforms of the respective elements is added for focusing within an object in both transmission and reception.

Although the spatial resolution of approximately 0.13 mm in the depth direction can be achieved by using the pulse echo method as described above, there are demands for higher spatial resolution. For example, if the layer structure in a blood vessel wall of a carotid artery can be observed in further detail, there would supposedly be a contribution to early detections of arteriosclerosis or the like.

A technique of improving the spatial resolution in such depth direction, i.e., direction in which an ultrasound wave is transmitted and received, is described in Japanese Patent Application Laid-open No. 2010-183979 and "Hirofumi Taki, Kousuke Taki, Takuya Sakamoto, Makoto Yamakawa, Tsuyoshi Shiina and Toru Sato: Conf Proc IEEE Eng Med Biol Soc. 2010; 1:5298-5301." In these documents, frequency domain interferometry (FDI) and Capon method that is adaptive signal processing are applied, and the result of visualizing a blood vessel is shown.

As described above, a general ultrasound wave diagnostic apparatus forms an image by acquiring an envelope of the received waveform for each scanning line. In the case of further improving the spatial resolution in the depth direction by applying FDI and the Capon method to the received waveform, the existence of a plurality of reflection layers is expected in a range of signals in the depth direction (within processing range) that is cut out in order to perform processing of FDI. In the case where a plurality of close reflection layers exist, there is a high possibility that reflected waves from the reflection layers have a high correlation with each other in the pulse echo method, since reflected waves with respect to one transmission waveform are received. It is known that, when adaptive signal processing of the Capon method or the like is directly applied with respect to a plurality of reflection waveforms having a high correlation in this manner, an unexpected behavior such as cancelling out a desired signal is performed. In order to reduce and prevent such influence by a signal having correlation (correlative interference wave), there is an approach of using the frequency averaging technique in combination. Accordingly, it is possible to apply FDI and the Capon method with respect to a signal obtained with the general pulse echo method.

Patent Literature 1: Japanese Patent Application Laid-open No. 2010-183979

Non Patent Literature 1: Hirofumi Taki, Kousuke Taki, Takuya Sakamoto, Makoto Yamakawa, Tsuyoshi Shiina and Toru Sato: Conf Proc IEEE Eng Med Biol Soc. 2010; 1:5298-5301

SUMMARY OF THE INVENTION

Upon application of FDI and adaptive signal processing of the Capon method or the like to a signal acquired by the pulse echo method as described above, there are cases where the effect of reduction in the influence of a correlative interference wave by the frequency averaging technique is insufficient. In such cases, there is a possibility of a change (decrease in particular) in an estimated power value (output value) in the result of applying FDI and adaptive signal processing.

The present invention has been made in view of a problem described above, and it is an object to provide an object information acquiring apparatus that can present an image with a stable and reduced influence of a correlative interference wave.

The present invention provides an object information acquiring apparatus comprising:

a plurality of converting elements with which an acoustic wave is transmitted to an object and the acoustic wave reflected within the object is received and converted into a plurality of received signals;

a processor that acquires, using the plurality of received signals, a power intensity signal showing a distribution of power intensity in a plurality of positions within the object through processing using frequency domain interferometry to which adaptive signal processing is applied; and a corrector that performs correction processing on the power intensity signal, the processor being configured to calculate a plurality of correlation values of frequency components using the plurality of received signals, perform frequency average processing on a correlation matrix that is a set of the plurality of calculated correlation values to acquire a first power intensity signal using a plurality of values obtained by the frequency average processing, and perform processing of reducing variance of elements in a diagonal direction of the correlation matrix using the plurality of calculated correlation values to acquire a second power intensity signal using the plurality of values subjected to this processing, and the corrector being configured to output a power intensity signal subjected to correction processing using the first power intensity signal and the second power intensity signal.

The present invention also provides an object information acquiring apparatus comprising:

a plurality of converting elements with which an acoustic wave is transmitted to an object and the acoustic wave reflected within the object is received and converted into a plurality of received signals;

a processor that acquires, using the plurality of received signals, a power intensity signal showing a distribution of power intensity in a plurality of positions within the object through processing using frequency domain interferometry to which adaptive signal processing is applied; and a corrector that performs correction processing on the power intensity signal, the processor being configured to calculate a plurality of correlation values of frequency components using the plurality of received signals, perform frequency average processing on a correlation matrix that is a set of the plurality of calculated correlation values to acquire a first power intensity signal using a plurality of values obtained by the frequency average processing, and perform processing of reducing variance of at least elements in a diagonal direction out of the plurality of values obtained by the frequency average processing to acquire a second power intensity signal using the plurality of values subjected to this processing, and the corrector being configured to output a power intensity signal subjected to correction processing using the first power intensity signal and the second power intensity signal.

The present invention also provides an object information acquiring apparatus comprising:

a plurality of converting elements with which an acoustic wave is transmitted to an object and the acoustic wave reflected within the object is received and converted into a plurality of received signals;

a processor that acquires, using the plurality of received signals, a power intensity signal showing a distribution of power intensity in a plurality of positions within the object through processing using frequency domain interferometry to which adaptive signal processing is applied; and a corrector that performs correction processing on the power intensity signal, the processor being configured to calculate a plurality of correlation values of frequency components using the plurality of received signals, perform frequency average processing on a correlation matrix that is a set of the plurality of calculated correlation values to acquire a first power intensity signal using a plurality of values obtained by the frequency average processing, and perform processing of reducing variance of elements in a diagonal direction of the correlation matrix using the plurality of calculated correlation values to acquire a second power intensity signal using the plurality of values subjected to this processing and the plurality of values obtained by the frequency average processing, and the corrector being configured to output a power intensity signal subjected to correction processing using the first power intensity signal and the second power intensity signal.

The present invention also provides a control method for an object information acquiring apparatus including a plurality of converting elements with which an acoustic wave is transmitted to an object and the acoustic wave reflected within the object is received and converted into a plurality of received signals, a processor that acquires, using the plurality of received signals, a power intensity signal showing a distribution of power intensity in a plurality of positions within the object through processing using frequency domain interferometry to which adaptive signal processing is applied, and a corrector that performs correction processing on the power intensity signal, the control method comprising the steps of:

calculating, with the processor, a plurality of correlation values of frequency components using the plurality of received signals;

performing, with the processor, frequency average processing on a correlation matrix that is a set of the plurality of calculated correlation values to acquire a first power intensity signal using a plurality of values obtained by the frequency average processing;

performing, with the processor, processing of reducing variance of elements in a diagonal direction of the correlation matrix using the plurality of calculated correlation values to acquire a second power intensity signal using the plurality of values subjected to this processing; and outputting, with the corrector, a power intensity signal subjected to correction processing using the first power intensity signal and the second power intensity signal.

The present invention also provides a control method for an object information acquiring apparatus including a plurality of converting elements with which an acoustic wave is transmitted to an object and the acoustic wave reflected within the object is received and converted into a plurality of received signals, a processor that acquires, using the plurality of received signals, a power intensity signal showing a distribution of power intensity in a plurality of positions within the object through processing using frequency domain interferometry to which adaptive signal processing is applied, and a corrector that performs correction processing on the power intensity signal, the control method comprising the steps of:

calculating, with the processor, a plurality of correlation values of frequency components using the plurality of received signals;

performing, with the processor, frequency average processing on a correlation matrix that is a set of the plurality of calculated correlation values to acquire a first power intensity signal using a plurality of values obtained by the frequency average processing;

performing, with the processor, processing of reducing variance of at least elements in a diagonal direction out of the plurality of values obtained by the frequency average processing to acquire a second power intensity signal using the plurality of values subjected to this processing; and outputting, with the corrector, a power intensity signal subjected to correction processing using the first power intensity signal and the second power intensity signal.

The present invention also provides a control method for an object information acquiring apparatus including a plurality of converting elements with which an acoustic wave is transmitted to an object and the acoustic wave reflected within the object is received and converted into a plurality of received signals, a processor that acquires, using the plurality of received signals, a power intensity signal showing a distribution of power intensity in a plurality of positions within the object through processing using frequency domain interferometry to which adaptive signal processing is applied, and a corrector that performs correction processing on the power intensity signal, the control method comprising the steps of:

calculating, with the processor, a plurality of correlation values of frequency components using the plurality of received signals;

performing, with the processor, frequency average processing on a correlation matrix that is a set of the plurality of calculated correlation values to acquire a first power intensity signal using a plurality of values obtained by the frequency average processing;

performing, with the processor, processing of reducing variance of elements in a diagonal direction of the correlation matrix using the plurality of calculated correlation values to acquire a second power intensity signal using the plurality of values subjected to this processing and the plurality of values obtained by the frequency average processing; and outputting, with the corrector, a power intensity signal subjected to correction processing using the first power intensity signal and the second power intensity signal.

With the present invention, an object information acquiring apparatus that can present an image with a stable and reduced influence of a correlative interference wave can be provided.

Further features of the present invention will become apparent from the following description of exemplary embodiments with reference to the attached drawings.

DESCRIPTION OF THE EMBODIMENTS

A preferred embodiment of the present invention will be described below with reference to the drawings. Note that the dimension, material, and shape of components, the relative arrangement thereof, and the like described below should be changed appropriately depending on the configuration of an apparatus or various conditions to which the invention is applied and are not intended to limit the scope of this invention to the description below.

In the present invention, an ultrasound wave refers to an elastic wave called a sound wave or acoustic wave. An object information acquiring apparatus of the present invention is an apparatus utilizing an ultrasound wave echo technique in which an ultrasound wave (acoustic wave) is transmitted to an object, a reflected wave (acoustic wave echo) reflected inside the object is received, and object information is acquired as image data. The acquired object information is morphological information that reflects the difference in acoustic impedance of tissues inside the object. A scanning line in the present invention indicates a virtual line formed in the proceeding direction of an ultrasound wave transmitted from a probe.

The object is typically a living body in medical ultrasound wave diagnosis, but this is not limiting.

Embodiment 1

Figure 1:
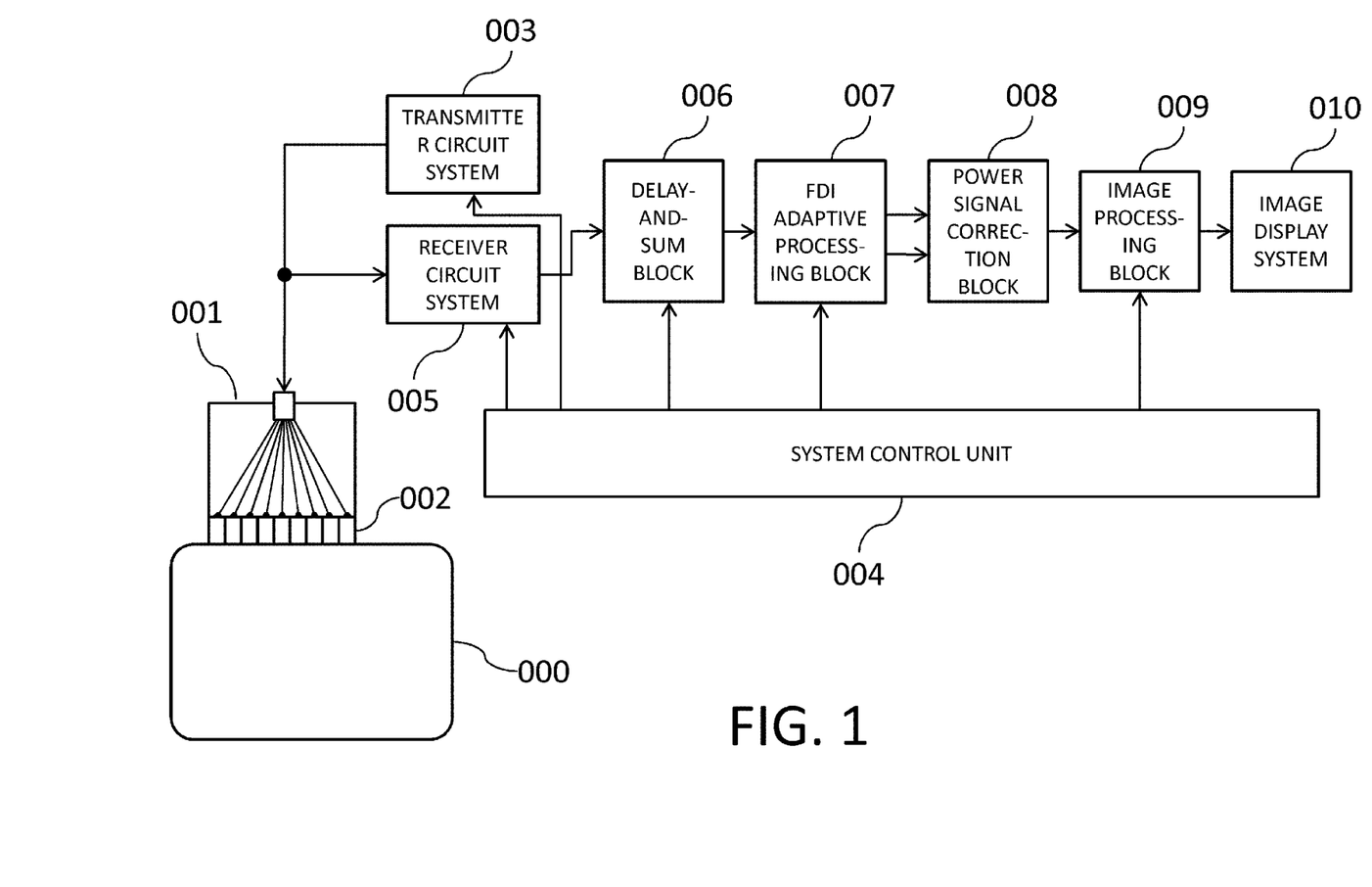
FIG. 1 is a diagram showing the system outline of an object information acquiring apparatus according to the present invention.

FIG. 1 is a diagram showing the system outline of an object information acquiring apparatus according to the present invention. The outline of configuration and behavior of the apparatus will be described using this diagram.

The apparatus includes a probe 001 including a plurality of ultrasound wave converting elements 002, a transmitter circuit system 003, a system control unit 004, and a receiver circuit system 005. The probe 001 is acoustically in contact with an object 000. The apparatus also includes a delay-and-sum block 006, an FDI adaptive processing block 007, a power signal correction block 008, an image processing block 009, and an image display system 010.

At the time of ultrasound wave transmission, the transmitter circuit system 003 creates a voltage waveform having a delay time or amplitude according to the position under attention or direction under attention, in accordance with a control signal from the system control unit 004. The voltage waveform is converted into an ultrasound wave by the plurality of ultrasound wave converting elements 002 and transmitted into the object from the probe 001. The ultrasound wave is reflected inside the object 000. The ultrasound wave converting element corresponds to a converting element of the present invention.

At the time of ultrasound wave reception, the reflected wave is converted into a plurality of voltage signals and input as a received signal to the receiver circuit system 005 by the plurality of ultrasound wave converting elements 002. The plurality of voltage signals are amplified and converted into a plurality of digital signals (digitized received signals) by the receiver circuit system 005. The digital signal output from the receiver circuit system 005 is input to the delay-and-sum block 006. In the present invention, not only an analog received signal output by the ultrasound wave converting element 002 but also a signal for which processing such as amplification or digital conversion has been performed is also expressed as received signal.

The delay-and-sum block 006 executes delay-and-sum processing, i.e., processing in which delay processing with respect to a plurality of digital signals is performed for addition in accordance with the direction or position of ultrasound wave transmission. A plurality of scanning line signals obtained by the delay-and-sum processing are input to the FDI adaptive processing block 007. On one scanning line, the plurality of scanning line signals are arranged. In a B-mode image displayed with a general ultrasound wave apparatus, an envelope of the scanning line signals is arranged for a plurality of scanning lines.

With respect to the input scanning line signal, the FDI adaptive processing block 007 performs processing using frequency domain interferometry (FDI) to which adaptive signal processing is applied. The FDI adaptive processing block corresponds to a processor of the present invention.

Figure 2:
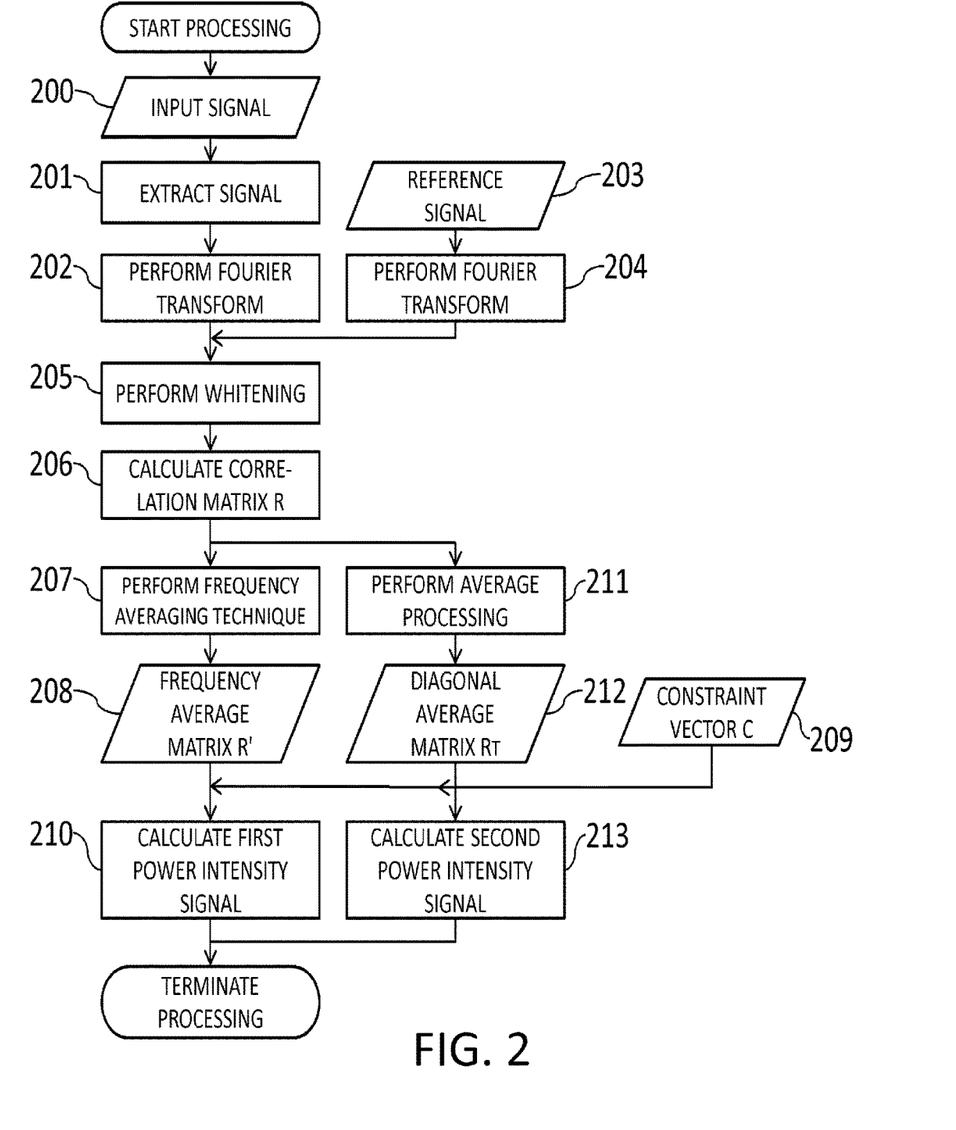
FIG. 2 is a diagram illustrating processing within an FDI adaptive processing block according to Embodiment 1.

Using FIG. 2, processing inside the FDI adaptive processing block 007 will be described. FIG. 2 shows the flow of operation in the processing, together with a signal or matrix used or calculated in the processing.

The frequency domain interferometry (FDI) is a method in which a received signal is decomposed for each frequency, the phase of the decomposed signal is changed in accordance with the position under attention, and the received power in the position under attention is estimated. The change amount of phase can be determined in advance from the product of the distance from a certain reference position to the position under attention and the wave number corresponding to the frequency.

In accordance with a received signal, adaptive signal processing adaptively changes the processing parameter thereof. The Capon method that is one form of adaptive signal processing is a method of processing in which, with respect to a plurality of input signals, power is minimized in a state where the sensitivity relating to the position under attention is fixed. That is, with a combination of FDI and adaptive signal processing, the received power in the position under attention is estimated using, with respect to the received signal decomposed into each frequency component, not the phase change amount or weight determined in advance but the phase change amount or weight calculated in accordance with the signal by adaptive signal processing.

The FDI adaptive processing block 007 receives a synthesis scanning line signal output from the delay-and-sum block 006 as an input signal (corresponding to reference numeral 200 in FIG. 2). (Hereinafter, reference numerals will be shown in parenthesis in a similar manner.) Then, a signal corresponding to a time to be processed in one time, i.e., corresponding to a processing range, is extracted from the input signal (201). Through Fourier transform, the extracted signal is divided into components ($X_{s1}$, $X_{s2}$, $X_{s3}$, ..., $X_{sN}$) for each frequency (202).

Meanwhile, the FDI adaptive processing block 007 receives a reference signal (203) from the system control unit. Through Fourier transform, the reference signal is divided into components ($X_{r1}$, $X_{r2}$, $X_{r3}$, ..., $X_{rN}$) for each frequency (204). In the case where a reference wave is held as frequency information, a Fourier conversion block 204 is unnecessary.

Next, the FDI adaptive processing block 007 performs whitening processing (205) shown by formula (1) below. The whitening processing is performed, for example, by division of respective frequency components of the input signal and the reference signal.

[Math. 1]

$$X_{wk} = \frac{X_{sk} X_{rk}^*}{|X_{rk}|^2 + \eta} \quad (1)$$

Herein, $X_{wk}$ (k=1, 2, ..., N) indicates components of respective frequencies after the whitening processing, $\eta$ a minute quantity for stabilization, and * a complex conjugate.

Formula (2) shows a vector X formed of each frequency component subjected to the whitening processing. Using this, the FDI adaptive processing block 007 calculates a correlation matrix R (206) as shown in formula (3). The correlation matrix R is a set of a plurality of correlation values calculated using the frequency components. The correlation value is obtained, for example, by multiplication of the frequency components.

[Math. 2]

$$X = [X_{w1}, X_{w2}, ..., X_{wN}]^T \quad (2)$$

$$R = XX^{T*} \quad (3)$$

Note that T indicates transposition. The correlation matrix R is a matrix having a size of N×N.

Next, the FDI adaptive processing block 007 carries out the frequency averaging technique in which a plurality of submatrices Rm of a predetermined size are extracted from the correlation matrix R and the submatrices are averaged (207).

[Math. 3]

$$R' = \frac{1}{M} \sum_{m=1}^{M} R_m \quad (4)$$

$$R_{mij} = X_{W(i+m-1)} X_{W(j+m-1)}^* \quad (5)$$

In formula (4), R' shows a frequency average matrix. Also, $R_m$ is a submatrix of the correlation matrix R and has $R_{mij}$ as an element. The element $R_{mij}$ is shown in formula (5). In the frequency averaging technique shown with formula (4), weighted averaging with weight in each submatrix may be carried out.

With this frequency average processing, the frequency average matrix R' (208) including a plurality of calculated average values is calculated.

Figure 8:
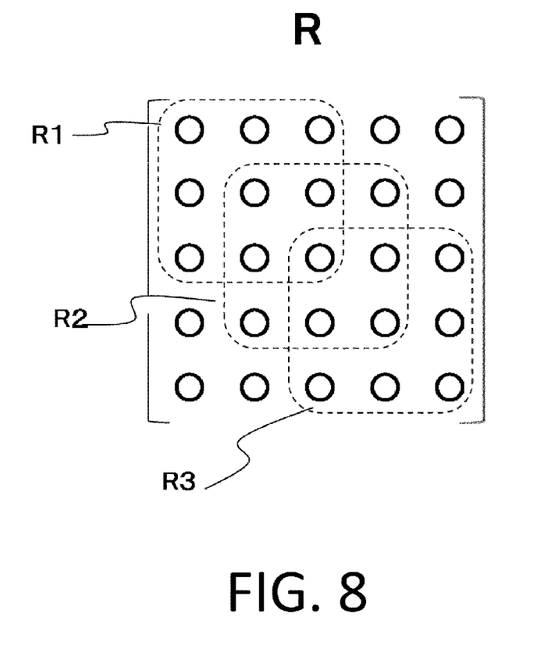
FIG. 8 is a diagram illustrating processing of calculating a frequency average matrix R'.

The processing will be described using FIG. 8. In the processing, submatrices R1, R2, and R3 arranged in the diagonal direction are extracted from the correlation matrix R of N×N (5×5 herein), and an average of the submatrices is calculated. The size of the submatrix may be arbitrary, as long as the number of elements is smaller than the number of elements in the correlation matrix.

The correlation matrix R, the submatrix Rm, and the frequency average matrix R' are all a Hermitian matrix. Therefore, it is possible to carry out the present invention by performing only the calculation of elements included in an upper triangular matrix or lower triangular matrix including on-diagonal elements. That is, it is possible to carry out processing equivalent to the processing described above regardless of the shape of a matrix.

Returning to FIG. 2, description will be continued. Using the elements of the correlation matrix R, the FDI adaptive processing block 007 carries out average processing of averaging the elements in the diagonal direction (211).

[Math. 4]

$$R_{Ti,j} = \begin{cases} \frac{1}{N+i-j} \sum_{m=1}^{N+i-j} R_{m,(m-i+j)} & (i \leq j) \\ R_{Tj,i}^* & (i > j) \end{cases} \quad (6)$$

In formula (6), $RT_{i,j}$ is an (i,j) element of a diagonal average matrix $R_T$ obtained by diagonal frequency averaging processing. In this manner, the diagonal average matrix $R_T$ (212) is calculated. In the average processing shown in formula (6), weighted averaging with weight in each element of the correlation matrix may be carried out.

Figure 5A:
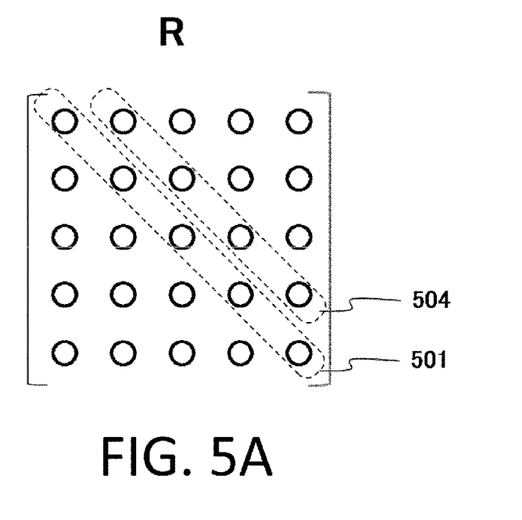
FIGS. 5A and 5B are diagrams illustrating processing of calculating a diagonal average matrix $R_T$.
Figure 5B:
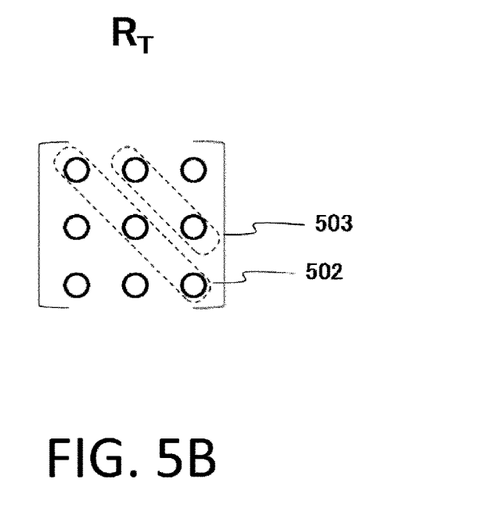

FIGS. 5A and 5B are diagrams for illustrating the concept of the average processing. FIG. 5A shows the correlation matrix R, and FIG. 5B the diagonal average matrix $R_T$.

Diagonal elements 502 (where i=j) of the diagonal average matrix $R_T$ are calculated by simple averaging of diagonal elements 501 of the correlation matrix R in which the number of elements is N×N, and the same value is substituted for in the diagonal elements 502.

An element group 503 (where i+1=j) in the diagonal direction in the upper triangular matrix of the diagonal average matrix $R_T$ is calculated by simple averaging of an element group 504 in the diagonal direction of the correlation matrix R, and the same value is substituted for in the element group 503 in the diagonal direction.

Note that i≤j≤N. The size of the diagonal average matrix $R_T$ may be an arbitrary size of N×N or smaller. For example, the size of the diagonal average matrix $R_T$ may be equivalent to the size of the frequency average matrix $R'$.

In the frequency average matrix $R'$ calculated in a manner described above, there is variance in the elements in the diagonal direction due to the existence of a correlative interference wave or the like. The diagonal average matrix $R_T$ having a constant value in the diagonal direction does not have variance in the diagonal direction.

Again, returning to FIG. 2, description will be continued. A constraint vector C is a vector that changes in accordance with a position r (corresponding to the depth, i.e., distance from the surface of ultrasound wave transmission and reception) within the processing range. The constraint vector C is defined with the following formula (7) (209).

[Math. 5]

$$C=[\exp(jk_1 r), \exp(jk_2 r), \ldots, \exp(jk_{(N-M+1)} r)] \qquad (7)$$

The FDI adaptive processing block 007 uses the constraint vector C, the frequency average matrix $R'$, and the diagonal average matrix $R_T$ to calculate a first power intensity signal $P(r)$ and a second power intensity signal $P_T(r)$ within the processing range (210 and 213). The calculation method is shown in the following formula (8) and formula (9).

[Math. 6]

$$P(r) = \frac{1}{C^{T*}(R' + \eta' E)^{-1} C} \qquad (8)$$

$$P_T(r) = \frac{1}{C^{T*}(R_T + \eta' E)^{-1} C} \qquad (9)$$

Note that $\eta' E$ is added for stabilization of inverse matrix calculation, $\eta'$ is a constant or a value that changes in accordance with the value of $R'$, $R_T$, or the like, and E is an identity matrix. Note that $\eta'$ in formula (8) and $\eta'$ in formula (9) do not need to be the same value and may be different values.

If an unprocessed signal is not among the input signals, the processing is terminated. If there is an unprocessed signal, the processing is continued, returning to signal extraction (201).

In this manner, the FDI adaptive processing block 007 performs FDI and adaptive signal processing (Capon method herein) with the scanning line signal output from the delay-and-sum block 006 as the input signal, and outputs the first and second power intensity signals.

Figure 4:
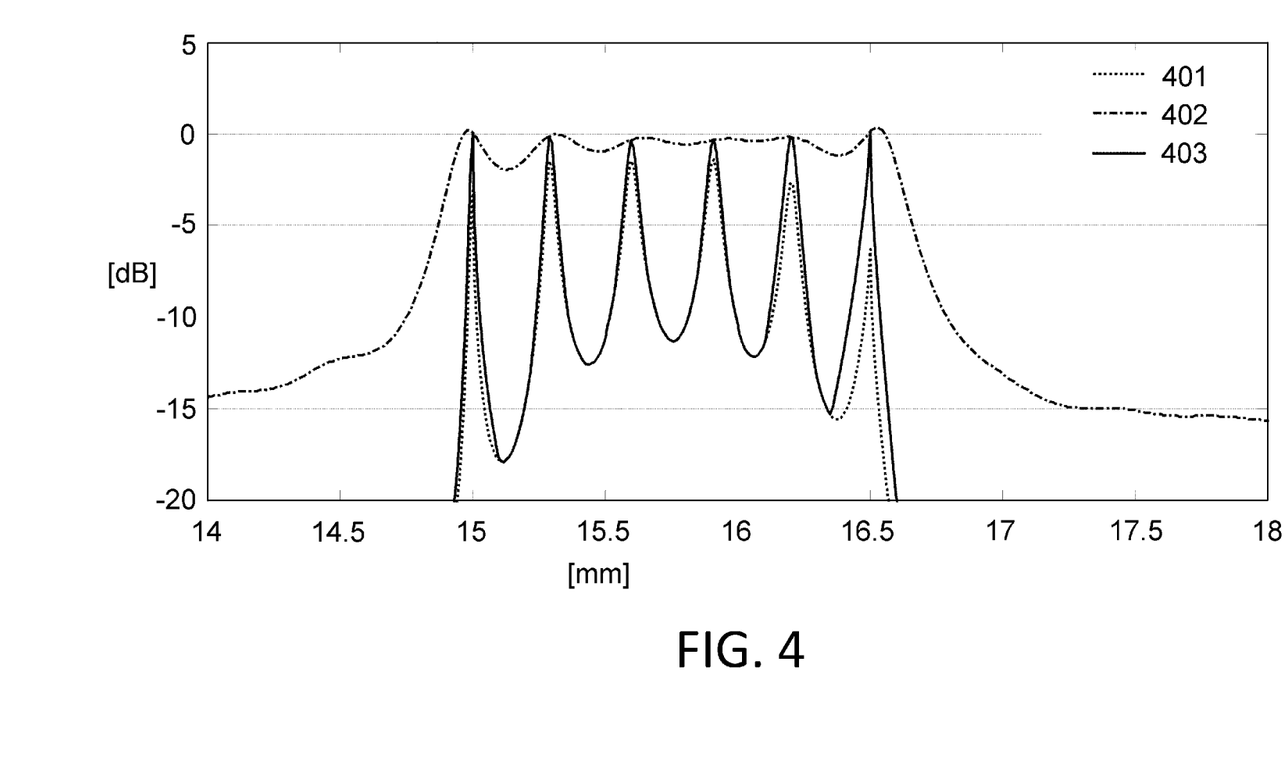
FIG. 4 is a diagram illustrating the effect of the present invention.

The first power intensity signal calculated from the frequency average matrix $R'$ and the second power intensity signal calculated from the diagonal average matrix $R_T$ will be described. While details will be described later, FIG. 4 shows the first power intensity signal and the second power intensity signal respectively with a dotted line (reference numeral 401) and a dashed-dotted line (reference numeral 402). FIG. 4 represents the distribution of the power intensity signal measured for a model.

The first power intensity signal is obtained as a result of performing FDI and adaptive signal processing with respect to the input scanning line signal. In the power intensity signal, the resolution in the depth direction is improved compared to a conventional imaging technique of acquiring an envelope.

As can been seen from the dotted line in a graph of FIG. 4, the first power intensity signal is high in spatial resolution, but may be influenced by a correlative interference wave.

The second power intensity signal is calculated using the diagonal average matrix $R_T$. The diagonal average matrix $R_T$ is a Toeplitz matrix in which elements in the diagonal direction match. The correlation matrix being in a state of the Toeplitz matrix indicates a state where a correlative interference wave is not within a distance range of performing the processing. That is, the average processing can be said to be processing of converting a correlative interference wave within the distance range of performing the average processing into an uncorrelated interference wave. Since there is almost not an influence of a correlative interference wave in the second power intensity signal calculated using the diagonal average matrix $R_T$ for which such average processing has been performed, it is possible to perform power intensity estimation of a position in which a reflector exists with higher precision.

Due to the existence of an uncorrelated interference wave, the spatial resolution is decreased compared to the first power intensity signal in which normal FDI and adaptive signal processing have been used. Such characteristics can be understood also from the dashed-dotted line shown in the graph of FIG. 4.

Returning to FIG. 1, description on the outline of the apparatus will be continued.

The first power intensity signal and the second power intensity signal are input to the power signal correction block 008. The power signal correction block 008 performs correction processing using the first power intensity signal and the second power intensity signal. Specifically, a power intensity signal of a position of the reflector (peak position where the power intensity is greater than a predetermined power intensity) obtained from the first power intensity signal is corrected with the second power intensity signal. The power signal correction block corresponds to a corrector of the present invention.

Figure 3:
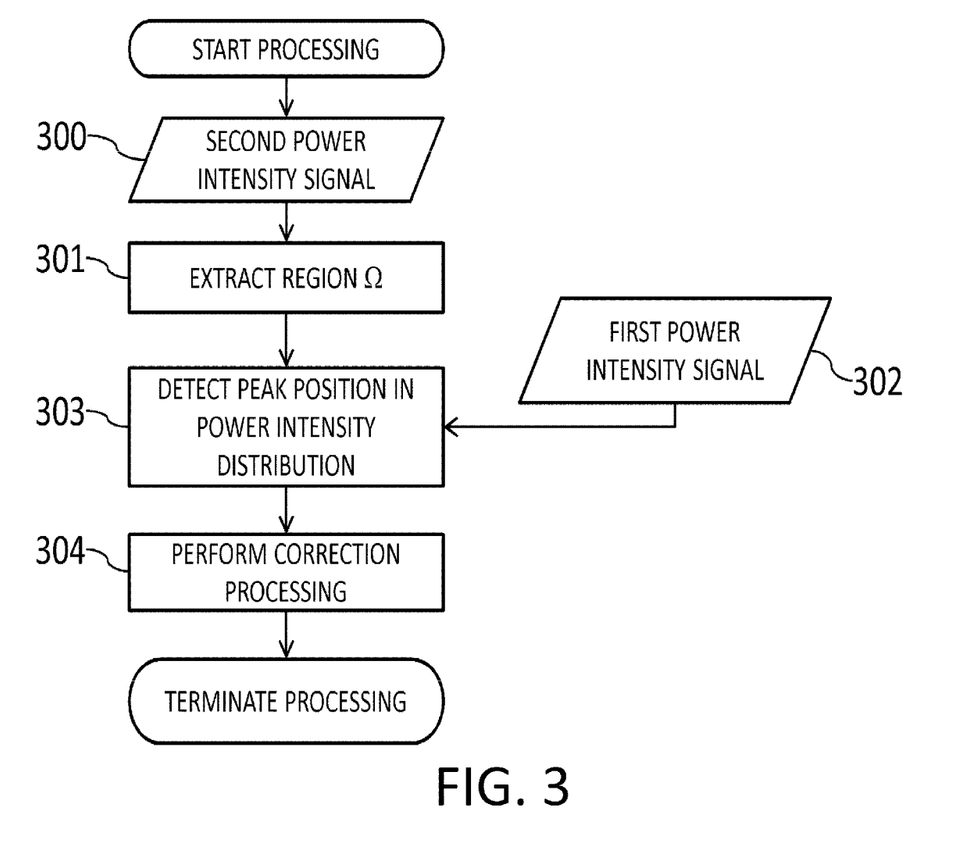
FIG. 3 is a diagram illustrating processing within a power signal correction block.

One example of a correction method is shown using FIG. 3. FIG. 3 shows the flow of operation in the correction processing, together with a signal used in the processing.

The power signal correction block 008 extracts a region $\Omega$ in which the second power intensity signal (corresponding to reference numeral 300 in FIG. 3) is higher than average (301).

Next, a position where the first power intensity signal (302) has a peak in the region $\Omega$ is detected (303).

With a detected l-th peak position as $r_{pl/2}$, a corrected power intensity signal to be calculated with the following formula (10) is calculated.

[Math. 7]

$$I_{cmp} = \max_{l} \left[ \frac{I_c(r) I_T(r_{pl})}{I_c(r_{pl})} \exp\left\{ -\log 2 \left( \frac{r_{pl} - r}{r_0} \right)^2 \right\} \right] \qquad (10)$$

Herein, $I_c(r)$ and $I_T(r)$ are respectively the first power intensity signal and the second power intensity signal, and $r_0$ is a positive number. Also, $I_c(r)$ is used in the case where $I_{cmp}(r) < I_c(r)$.

The corrected power intensity signal output from the power signal correction block 008 is input to the image processing block 009. In accordance with a command from the system control unit 004, the image processing block 009 performs various image processing such as edge reinforcement or contrast adjustment, and creates and outputs image display data. The image display system 010 displays the input image display data.

The outline of the object information acquiring apparatus according to the present invention has been given above.

Next, using FIG. 4, the effect of the present invention will be described.

FIG. 4 is the processing result of applying the present invention with respect to a model in which there are reflection layers every 0.3 mm. The abscissa represents the position (mm) on the object, and the ordinate the signal intensity (dB) in each position. FIG. 4 shows the distribution of the measure power intensity signal. In the figure, the dotted line shows the processing result of using FDI and adaptive signal processing for a received signal, i.e., the first power intensity signal (reference numeral 401). The dashed-dotted line shows the second power intensity signal (reference numeral 402) calculated using the diagonal average matrix $R_T$.

First, the first power intensity signal shown by the dotted line will be brought to attention. It can be seen that the first power intensity signal is high in spatial resolution. While the reflection layer is adjusted such that the reflection intensity is 0 dB, there are portions in the processing result where the reflection intensity is approximately −6 dB, and it can be seen that the power estimation precision is decreased by the influence of a correlative interference wave or the like.

Next, the second power intensity signal shown by the dashed-dotted line will be brought to attention. Since the second power intensity signal is an uncorrelated interference wave converted from a correlative interference wave, the effect of improvement in spatial resolution by adaptive signal processing is obtained less than with the first power intensity signal. However, since the influence of a correlative interference wave is significantly reduced, the power intensity value of the reflection intensity is closer to 0 dB that is a setting value. That is, although the spatial resolution has decreased, the estimation precision for the reflected power intensity in the position where the reflection layer exists is improved.

A solid line in FIG. 4 is the corrected power intensity (reference numeral 403) calculated using the first power intensity signal and the second power intensity signal. From the corrected power intensity, it can be seen that the spatial resolution is high, and the power intensity value of the reflection intensity is closer to the true value (0 dB).

By applying the present invention in this manner, the influence of a correlative interference wave or the like can be reduced to obtain an image in which precision of the estimated power value has been improved.

The diagonal average matrix $R_T$ has been described as a Toeplitz matrix. However, the effect of the present invention is obtained, as long as variance in an element group (such as, for example, 502 or 503) in the diagonal direction of the diagonal average matrix $R_T$ is smaller than in the normal frequency average matrix R'.

The correction with the first power intensity signal and the second power intensity signal is not limited to the approach shown herein. Means of correction using the high spatial resolution in the first power intensity signal and the high power estimation precision in the second power intensity signal suffices. By performing such correction, the effect of the present invention is obtained.

Embodiment 2

Embodiment 2 of the present invention will be described, focusing on portions different from the embodiment described above.

Figure 6:
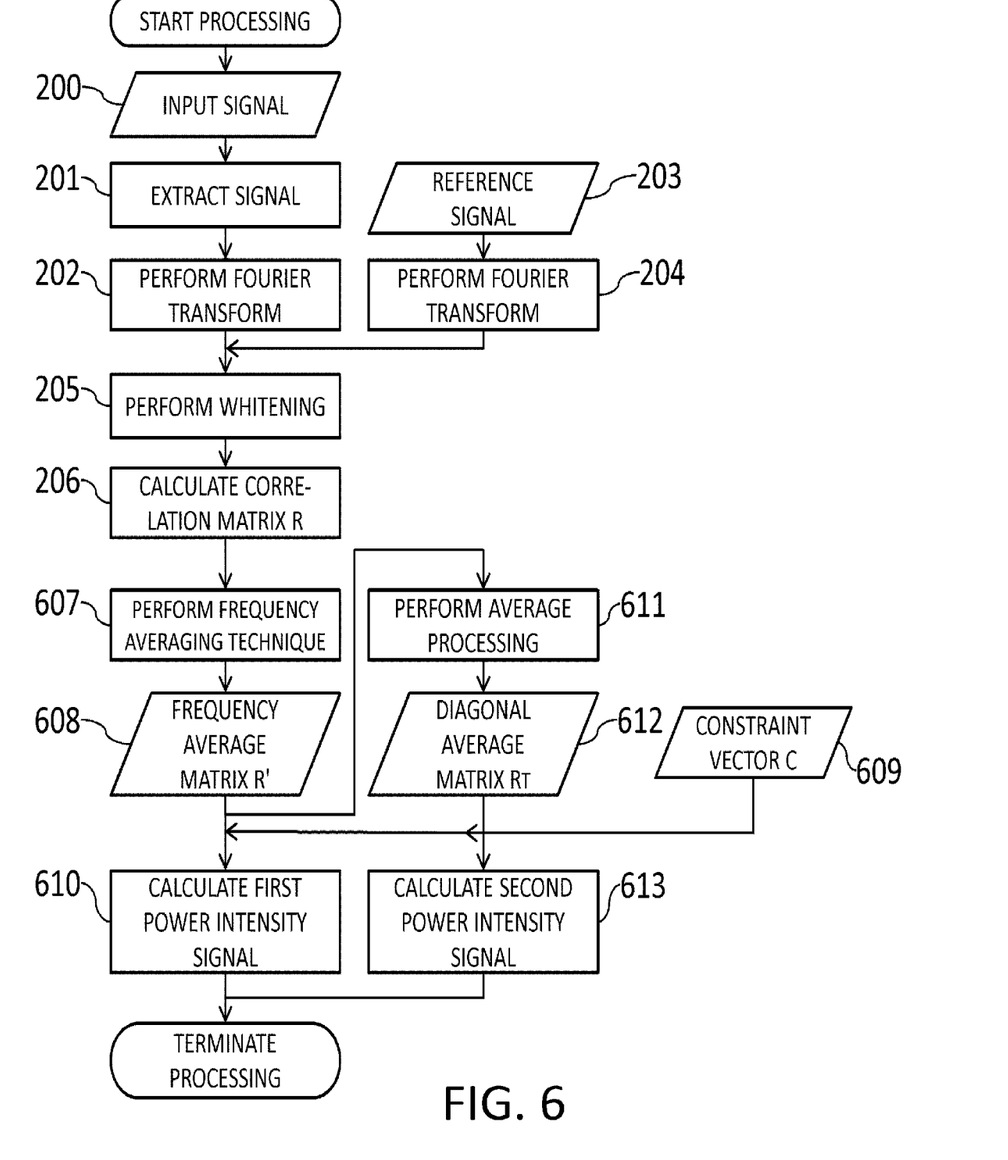
FIG. 6 is a diagram illustrating processing within an FDI adaptive processing block according to Embodiment 2.

In this embodiment, processing inside the FDI adaptive processing block 007 differs. FIG. 6 is a diagram showing the flow of the processing within the FDI adaptive processing block 007 in this embodiment. From the start of processing up to the calculation of the correlation matrix R (206) is similar to the embodiment described above, and therefore description is omitted.

The FDI adaptive processing block 007 performs processing with the frequency averaging technique (607). Accordingly, the frequency average matrix R' is calculated (608). The frequency average matrix R' is obtained by formula (11). The element $R_{mij}$ of the submatrix $R_m$ used at this time is shown in formula (12). In the frequency averaging technique shown with formula (11), weighted averaging with weight in each submatrix may be carried out.

[Math. 8]

$$R' = \frac{1}{M}\sum_{m=1}^{M} R_m \qquad (11)$$

$$R_{mij} = X_{W(i+m-1)} X^*_{W(j+m-1)} \qquad (12)$$

Next, in this embodiment, the frequency average matrix R' is used upon performing average processing (611). Accordingly, the diagonal average matrix $R_T$ is calculated (612).

Herein, K is the number of elements included in one column of the frequency average matrix R'.

[Math. 9]

$$R_{Ti,j} = \begin{cases} \dfrac{1}{K+i-j}\sum_{m=1}^{K+i-j} R'_{m,(m-i+j)} & (i \le j) \\ R^*_{Tj,i} & (i > j) \end{cases} \qquad (13)$$

Then, the FDI adaptive processing block 007 calculates the first power intensity signal and the second power intensity signal (610 and 613) using the frequency average matrix R', the diagonal average matrix $R_T$, and the constraint vector C (609). In the average processing shown in formula (13), weighted averaging with weight in each element of the frequency average matrix may be carried out.

Processing thereafter is similar to the embodiment described above, and therefore is omitted.

With this embodiment, the diagonal average matrix $R_T$ can be calculated with a smaller processing scale than when the average processing is performed directly from the correlation matrix $R_T$. Therefore, circuit scale reduction, cost reduction, and time reduction are expected. The diagonal average matrix $R_T$ obtained herein is a Toeplitz matrix, and an image in which the influence of a correlative interference wave is reduced can be obtained in a similar manner to the embodiment described above.

Embodiment 3

Embodiment 3 of the present invention will be described, focusing on portions different from the respective embodiments described above.

Figure 7:
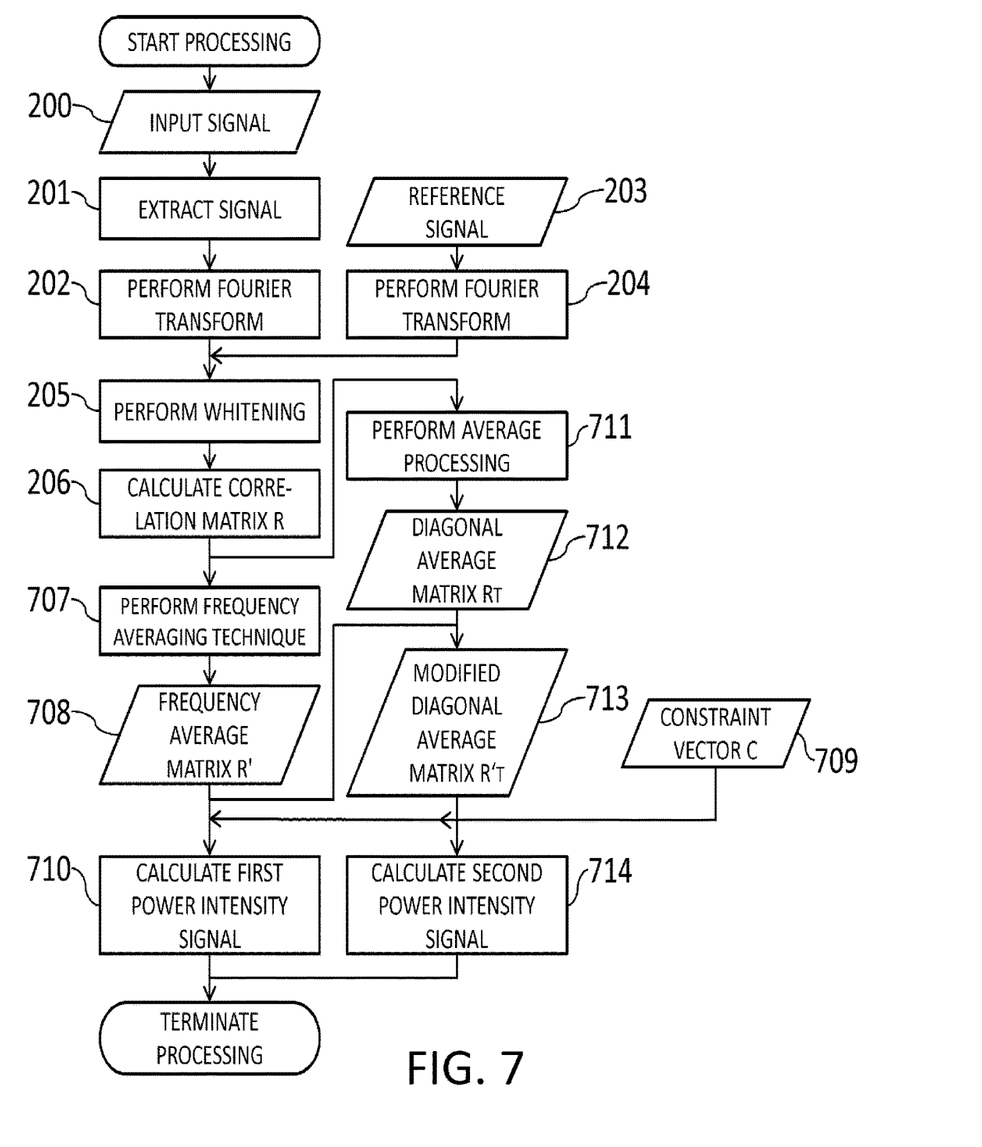
FIG. 7 is a diagram illustrating processing within an FDI adaptive processing block according to Embodiment 3.

In this embodiment, processing inside the FDI adaptive processing block 007 differs. FIG. 7 is a diagram showing the flow of the processing within the FDI adaptive processing block 007 in this embodiment. From the start of processing up to the calculation of the correlation matrix R (206) is similar to the embodiment described above, and therefore description is omitted.

The FDI adaptive processing block 007 performs processing with the frequency averaging technique (707). Accordingly, the frequency average matrix R' is calculated (708). The frequency average matrix R' is obtained by formula (14). The element $R_{mij}$ of the submatrix $R_m$ used at this time is shown in formula (15). In the frequency averaging technique shown with formula (14), weighted averaging with weight in each submatrix may be carried out.

[Math. 10]

$$R' = \frac{1}{M}\sum_{m=1}^{M} R_m \quad (14)$$

$$R_{mij} = X_{W(i+m-1)}X^*_{W(j+m-1)} \quad (15)$$

The FDI adaptive processing block 007 uses the elements of the correlation matrix R to carry out average processing of averaging the same in the diagonal direction (711). This is shown in formula (16).

[Math. 11]

$$R_{Ti,j} = \begin{cases} \dfrac{1}{N+i-j}\displaystyle\sum_{m=1}^{K+i-j} R_{m,(m-i+j)} & (i \leq j) \\ R^*_{Tj,i} & (i > j) \end{cases} \quad (16)$$

Accordingly, the diagonal average matrix $R_T$ is calculated (712). In the average processing shown with formula (16), weighted averaging with weight in the elements of the correlation matrix may be carried out.

Next, the FDI adaptive processing block 007 calculates a modified diagonal average matrix $R'_T$ (713) by synthesizing the frequency average matrix R' and the diagonal average matrix $R_T$ as shown in formula (17).

[Math. 12]

$$R'_T = (1-\alpha)R' + \alpha R_T \quad (17)$$

A synthesis ratio α is a coefficient (weight) used for calculation and takes a value of 0 or greater and 1 or less.

Then, the FDI adaptive processing block 007 calculates a first power intensity signal 710 and a second power intensity signal 714 (710 and 714) using the frequency average matrix R', the modified diagonal average matrix $R'_T$, and the constraint vector C (709). Calculation processing is performed as shown in formula (18) and formula (19). Note that η' in formula (18) and η' in formula (19) do not need to be the same value and may be different values.

[Math. 13]

$$P(r) = \frac{1}{C^{T*}(R' + \eta' E)^{-1}C} \quad (18)$$

$$P_T(r) = \frac{1}{C^{T*}(R'_T + \eta' E)^{-1}C} \quad (19)$$

Processing thereafter is similar to the respective embodiments described above, and therefore is omitted.

The modified diagonal average matrix $R'_T$ will be described. In the diagonal average matrix $R_T$ that is a Toeplitz matrix, the variance of an element group in the diagonal direction is 0. In the frequency average matrix R', on the other hand, there is variance in an element group in the diagonal direction, in the case where a coherent scattered wave exists within the processing range. In the modified diagonal average matrix $R'_T$ in which these matrices are weighted and added, variance of an element group in the diagonal direction is smaller than at least in the frequency average matrix R'.

Therefore, in the second power intensity signal calculated using the modified diagonal average matrix $R'_T$, the influence of a correlative interference wave is reduced than in the first power intensity signal. That is, power intensity estimation can be performed with higher precision than with the first power intensity signal.

Thus, the effect of the present invention can be obtained in this embodiment as well.

In this embodiment, the diagonal average matrix $R_T$ calculated using the average processing for the correlation matrix R has been synthesized with the frequency average matrix R'. However, the effect of the present invention is obtained also when the diagonal average matrix $R_T$ is calculated from the frequency average matrix R' and synthesized with the frequency average matrix R', in a similar manner to Embodiment 2.

In the object information acquiring apparatus having the configuration as described above, the system control unit 004, the delay-and-sum block 006, the FDI adaptive processing block 007, the power signal correction block 008, the image processing block 009, and the like can be configured by an information processing device. The present invention can also be understood as a control method in which the information processing device is caused to execute each process in the present invention. The present invention can also be understood as a program that causes execution of such a control method.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment (s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-010410, filed on Jan. 23, 2013, which is hereby incorporated by reference herein in its entirety.

What is claimed is:

1. An object information acquiring apparatus comprising:
a plurality of conversion elements configured to receive an acoustic wave reflected within the object and to output a plurality of received signals;
a first processor that acquires, using the plurality of received signals, a power intensity signal showing a distribution of power intensity in a plurality of positions within the object through processing using frequency domain interferometry to which adaptive signal processing is applied;
a corrector that performs correction processing on the power intensity signal to output a corrected power intensity signal; and
an image processor that outputs image display data based on the corrected power intensity signal,
wherein the first processor is configured to
calculate a plurality of correlation values of frequency components using the plurality of received signals,
perform frequency average processing on a correlation matrix that is a set of the plurality of calculated correlation values to acquire a first power intensity signal using a plurality of values obtained by the frequency average processing, and
perform processing of reducing variance of elements in a diagonal direction of the correlation matrix by averaging at least one of super-diagonal and sub-diagonal elements using the plurality of calculated correlation values to acquire a second power intensity signal using the plurality of values subjected to this processing, and
wherein the corrector outputs the corrected power intensity signal using the first power intensity signal and the second power intensity signal.

2. The object information acquiring apparatus according to claim 1, wherein the first processor assumes a position in the first power intensity signal where power intensity is greater than a predetermined value as a position of a reflector within the object, and the corrector corrects a power intensity signal of the position of the reflector with the second power intensity signal.

3. The object information acquiring apparatus according to claim 1, wherein the first processor applies a Capon method as the adaptive signal processing.

4. The object information acquiring apparatus according to claim 1, wherein the first processor performs average processing of elements as the processing of reducing variance in elements when acquiring the second power intensity signal.

5. The object information acquiring apparatus according to claim 1, wherein the first processor is configured to perform processing of reducing the variance of elements in the diagonal direction of the correlation matrix using the plurality of calculated correlation values to acquire the second power intensity signal using the plurality of values subjected to this processing and the plurality of values obtained by the frequency average processing.

6. The object information acquiring apparatus according to claim 5, wherein the first processor assumes a position in the first power intensity signal where power intensity is greater than a predetermined value as a position of a reflector within the object, and the corrector corrects a power intensity signal of the position of the reflector with the second power intensity signal.

7. The object information acquiring apparatus according to claim 5, wherein the first processor applies a Capon method as the adaptive signal processing.

8. The object information acquiring apparatus according to claim 5, wherein the first processor performs average processing of elements as the processing of reducing variance in elements when acquiring the second power intensity signal.

9. The object information acquiring apparatus according to claim 1, wherein the averaging includes forming a weighted average.

10. An object information acquiring apparatus comprising:
a plurality of conversion elements configured to receive an acoustic wave reflected within the object and to output a plurality of received signals;
a first processor that acquires, using the plurality of received signals, a power intensity signal showing a distribution of power intensity in a plurality of positions within the object through processing using frequency domain interferometry to which adaptive signal processing is applied;
a corrector that performs correction processing on the power intensity signal to output a corrected power intensity signal; and
an image processor that outputs image display data based on the corrected power intensity signal,
the first processor being configured
to calculate a plurality of correlation values of frequency components using the plurality of received signals,
to perform frequency average processing on a correlation matrix that is a set of the plurality of calculated correlation values to acquire a first power intensity signal using a plurality of values obtained by the frequency average processing, and
to perform processing of reducing variance of at least elements in a diagonal direction out of the plurality of values obtained by the frequency average processing by averaging at least one of super-diagonal and sub-diagonal elements to acquire a second power intensity signal using the plurality of values subjected to this processing, and
the corrector being configured to output the corrected power intensity signal using the first power intensity signal and the second power intensity signal.

11. The object information acquiring apparatus according to claim 10, wherein the first processor assumes a position in the first power intensity signal where power intensity is greater than a predetermined value as a position of a reflector within the object, and the corrector corrects a power intensity signal of the position of the reflector with the second power intensity signal.

12. The object information acquiring apparatus according to claim 10, wherein the first processor applies a Capon method as the adaptive signal processing.

13. The object information acquiring apparatus according to claim 10, wherein the first processor performs average processing of elements as the processing of reducing variance in elements when acquiring the second power intensity signal.

14. The object information acquiring apparatus according to claim 10, wherein the averaging includes forming a weighted average.

15. A control method for an object information acquiring apparatus including a plurality of conversion elements configured to receive an acoustic wave reflected within the object and to output a plurality of received signals, a first processor that acquires, using a plurality of received signals obtained by receiving an acoustic wave reflected within the object using a plurality of conversion elements, a power intensity signal showing a distribution of power intensity in a plurality of positions within the object through processing using frequency domain interferometry to which adaptive signal processing is applied, a corrector that performs correction processing on the power intensity signal to output a corrected power intensity signal, and an image processor that outputs image display data based on the corrected power intensity signal, the control method comprising the steps of:
receiving, by the plurality of conversion elements, an acoustic wave reflected within the object and to output a plurality of received signals;
acquiring, by the first processor, using the plurality of received signals, a power intensity signal showing a distribution of power intensity in a plurality of positions within the object through processing using frequency domain interferometry to which adaptive signal processing is applied;
performing, by the corrector, correction processing on the power intensity signal to output a corrected power intensity signal; and
outputting, by the image processor, image display data based on the corrected power intensity signal,
wherein the acquiring comprises:
calculating, with the first processor, a plurality of correlation values of frequency components using the plurality of received signals;
performing, with the first processor, frequency average processing on a correlation matrix that is a set of the plurality of calculated correlation values to acquire a first power intensity signal using a plurality of values obtained by the frequency average processing; and
performing, with the first processor, processing of reducing variance of elements in a diagonal direction of the correlation matrix by averaging at least one of super-diagonal and sub-diagonal elements using the plurality of calculated correlation values to acquire a second power intensity signal using the plurality of values subjected to this processing; and
wherein the correcting comprises outputting, with the corrector, the corrected power intensity signal using the first power intensity signal and the second power intensity signal.

16. A control method according to claim 15, wherein the step of performing, with the first processor, processing of reducing variance of elements in the diagonal direction of the correlation matrix using the plurality of calculated correlation values to acquire the second power intensity signal using the plurality of values subjected to this processing is performed also using the plurality of values obtained by the frequency average processing.

17. A non-transitory computer-readable storage medium storing a program that causes an information processing device of an object information acquiring apparatus to execute each step in a control method, the apparatus including a plurality of conversion elements configured to receive an acoustic wave reflected within the object and to output a plurality of received signals, a first processor that acquires, using the plurality of received signals, a power intensity signal showing a distribution of power intensity in a plurality of positions within the object through processing using frequency domain interferometry to which adaptive signal processing is applied, a corrector that performs correction processing on the power intensity signal to output a corrected power intensity signal, and an image processor that outputs image display data based on the corrected power intensity signal, the control method comprising the steps of:
receiving, by the plurality of conversion elements, an acoustic wave reflected within the object and to output a plurality of received signals;
acquiring, by the first processor, using the plurality of received signals, a power intensity signal showing a distribution of power intensity in a plurality of positions within the object through processing using frequency domain interferometry to which adaptive signal processing is applied;
performing, by the corrector, correction processing on the power intensity signal to output a corrected power intensity signal; and
outputting, by the image processor, image display data based on the corrected power intensity signal,
wherein the acquiring comprises:
calculating, with the first processor, a plurality of correlation values of frequency components using the plurality of received signals;
performing, with the first processor, frequency average processing on a correlation matrix that is a set of the plurality of calculated correlation values to acquire a first power intensity signal using a plurality of values obtained by the frequency average processing; and
performing, with the first processor, processing of reducing variance of elements in a diagonal direction of the correlation matrix by averaging at least one of super-diagonal and sub-diagonal elements using the plurality of calculated correlation values to acquire a second power intensity signal using the plurality of values subjected to this processing; and
wherein the correcting comprises outputting a corrected power intensity signal subjected to correction processing using the first power intensity signal and the second power intensity signal.

18. A non-transitory computer-readable storage medium according to claim 17, wherein the step of performing processing of reducing variance of elements in the diagonal direction of the correlation matrix using the plurality of calculated correlation values to acquire the second power intensity signal using the plurality of values subjected to this processing is performed also using the plurality of values obtained by the frequency average processing.

19. A control method for an object information acquiring apparatus including a plurality of conversion elements configured to receive an acoustic wave reflected within the object and to output a plurality of received signals, a first processor that acquires, using the plurality of received signals, a power intensity signal showing a distribution of power intensity in a plurality of positions within the object through processing using frequency domain interferometry to which adaptive signal processing is applied, a corrector that performs correction processing on the power intensity signal to output a corrected power intensity signal, and an image processor that outputs image display data based on the corrected power intensity signal, the control method comprising the steps of:

receiving, by the plurality of conversion elements, an acoustic wave reflected within the object and to output a plurality of received signals;

acquiring, by the first processor, using the plurality of received signals, a power intensity signal showing a distribution of power intensity in a plurality of positions within the object through processing using frequency domain interferometry to which adaptive signal processing is applied;

performing, by the corrector, correction processing on the power intensity signal to output a corrected power intensity signal; and outputting, by the image processor, image display data based on the corrected power intensity signal, wherein the acquiring comprises:

calculating, with the first processor, a plurality of correlation values of frequency components using the plurality of received signals;

performing, with the first processor, frequency average processing on a correlation matrix that is a set of the plurality of calculated correlation values to acquire a first power intensity signal using a plurality of values obtained by the frequency average processing; and performing, with the first processor, processing of reducing variance of at least elements in a diagonal direction out of the plurality of values obtained by the frequency average processing by averaging at least one of super-diagonal and sub-diagonal elements to acquire a second power intensity signal using the plurality of values subjected to this processing; and wherein the correcting comprises outputting, with the corrector, the corrected power intensity signal using the first power intensity signal and the second power intensity signal.

20. A non-transitory computer-readable storage medium storing a program that causes an information processing device of an object information acquiring apparatus to execute each step in a control method, the apparatus including a plurality of conversion elements configured to receive an acoustic wave reflected within the object and to output a plurality of received signals, a first processor that acquires, using the plurality of received signals, a power intensity signal showing a distribution of power intensity in a plurality of positions within the object through processing using frequency domain interferometry to which adaptive signal processing is applied, a corrector that performs correction processing on the power intensity signal to output a corrected power intensity signal, and an image processor that outputs image display data based on the corrected power intensity signal, the control method comprising the steps of:

receiving, by the plurality of conversion elements, an acoustic wave reflected within the object and to output a plurality of received signals;

acquiring, by the first processor, using the plurality of received signals, a power intensity signal showing a distribution of power intensity in a plurality of positions within the object through processing using frequency domain interferometry to which adaptive signal processing is applied;

performing, by the corrector, correction processing on the power intensity signal to output a corrected power intensity signal; and outputting, by the image processor, image display data based on the corrected power intensity signal, wherein the acquiring comprises:

calculating, with the first processor, a plurality of correlation values of frequency components using the plurality of received signals;

performing, with the first processor, frequency average processing on a correlation matrix that is a set of the plurality of calculated correlation values to acquire a first power intensity signal using a plurality of values obtained by the frequency average processing; and performing, with the first processor, processing of reducing variance of elements in a diagonal direction of the correlation matrix by averaging at least one of super-diagonal and sub-diagonal elements using the plurality of calculated correlation values to acquire a second power intensity signal using the plurality of values subjected to this processing; and wherein the correcting comprises outputting a corrected power intensity signal subjected to correction processing using the first power intensity signal and the second power intensity signal.

\* \* \* \* \*